(12) United States Patent
Gocho

(10) Patent No.: US 7,290,440 B2
(45) Date of Patent: Nov. 6, 2007

(54) LEAK TESTER

(75) Inventor: Masanori Gocho, Hachioji (JP)

(73) Assignee: Olympus Corporation (JP)

( * ) Notice: Subject to any disclaimer, the term of this patent is extended or adjusted under 35 U.S.C. 154(b) by 0 days.

(21) Appl. No.: 10/940,786

(22) Filed: Sep. 14, 2004

(65) Prior Publication Data
US 2005/0056081 A1    Mar. 17, 2005

Related U.S. Application Data

(63) Continuation of application No. PCT/JP02/08740, filed on Aug. 29, 2002.

(30) Foreign Application Priority Data
Mar. 15, 2002 (JP) .............................. 2002-073088

(51) Int. Cl.
G01M 3/04 (2006.01)
(52) U.S. Cl. ...................................................... 73/49.2
(58) Field of Classification Search ............... 73/49.2, 73/40, 52; 702/51
See application file for complete search history.

(56) References Cited

U.S. PATENT DOCUMENTS

| | | | | |
|---|---|---|---|---|
| 2,833,141 A | * | 5/1958 | Holm ............................. | 73/40 |
| 2,936,611 A | * | 5/1960 | Le Mat et al. ................. | 73/49.2 |
| 3,800,586 A | * | 4/1974 | Delatorre et al. ............. | 73/49.2 |
| 3,893,332 A | | 7/1975 | Dolan et al. | |
| 4,587,619 A | * | 5/1986 | Converse et al. ............. | 702/51 |
| 4,670,847 A | * | 6/1987 | Furuse .......................... | 702/51 |
| 4,675,834 A | * | 6/1987 | Furuse .......................... | 702/51 |
| 4,686,638 A | * | 8/1987 | Furuse .......................... | 702/51 |
| 4,942,758 A | * | 7/1990 | Cofield ......................... | 73/49.2 |
| 4,993,256 A | * | 2/1991 | Fukuda ......................... | 73/49.2 |
| 5,239,859 A | * | 8/1993 | Lehmann ..................... | 73/49.2 |
| 5,367,797 A | * | 11/1994 | Zaim ........................... | 73/49.2 |
| 5,412,978 A | * | 5/1995 | Boone et al. ................. | 73/49.2 |
| 5,795,995 A | | 8/1998 | Shimaoka et al. | |
| 6,112,578 A | * | 9/2000 | Black et al. ................... | 73/40 |
| 6,182,501 B1 | * | 2/2001 | Furuse et al. ................. | 73/49.2 |
| 6,854,318 B2 | * | 2/2005 | Sagi et al. ..................... | 73/40 |

(Continued)

FOREIGN PATENT DOCUMENTS

CN    2144303 Y    10/1993

(Continued)

OTHER PUBLICATIONS

International Search Report dated Nov. 20, 2002.

(Continued)

*Primary Examiner*—Hezron Williams
*Assistant Examiner*—John Fitzgerald
(74) *Attorney, Agent, or Firm*—Ostrolenk, Faber, Gerb & Soffen, LLP

(57) ABSTRACT

A leak tester which detects leakage of a gas from a measured object, the leak tester including a source of a pressurized gas which supplies the pressurized gas, a differential pressure detecting section which detects a pressure difference between the pressure of a gas in the measured object and the pressure of a pressurized gas supplied by the source of the pressurized gas, and a pressure adjusting section which makes the pressure of the pressurized gas supplied by the source of the pressurized gas constant.

4 Claims, 6 Drawing Sheets

U.S. PATENT DOCUMENTS

2001/0032494 A1   10/2001   Greszler

FOREIGN PATENT DOCUMENTS

| JP | 63-121000 | 5/1988 |
| JP | 6-194257 | 7/1994 |
| JP | 8-15079 | 1/1996 |
| JP | 11-160190 | 6/1999 |
| JP | 2000-47503 | 2/2000 |
| JP | 2001-235386 | 8/2001 |

OTHER PUBLICATIONS

Letter from German associate dated Jul. 24, 2006 forwarding the Search Report dated Jun. 22, 2006 to Japanese associate, including discussion of relevancy thereof.

Search Report issued by European Patent Office on Jun. 22, 2006 in connection with corresponding European patent application NO. EP 02 76 5375.

Untranslated Chinese Action issued on Mar. 2, 2007 in connection with corresponding Chinese application No. 028285484.

English translation of Chinese Office Action issued in connection with 028285484 submitted in lieu of statement of relevancy of prior art teachings to the instant application.

Principle of, Calculation of and Test Research on Reduction of Airstream Pulsation by Orifice Plate, Feb. 28, 1979, *China Academic Journal Electronic Publishing House*, 1994-2007; http://www.cnki.net.

\* cited by examiner

LEAK TESTER

CROSS-REFERENCE TO RELATED APPLICATIONS

This is a Continuation Application of PCT Application No. PCT/JP02/08740, filed Aug. 29, 2002, which was published under PCT Article 21(2) in Japanese.

This application is based upon and claims the benefit of priority from prior Japanese Patent Application No. 2002-073088, filed Mar. 15, 2002, the entire contents of which are incorporated herein by reference.

BACKGROUND OF THE INVENTION

1. Field of the Invention

The present invention relates to a leak tester that senses leakage from an airtight article, for example, an endoscope.

2. Description of the Related Art

For example, an endoscope is a reusable medical apparatus and must thus be washed and disinfected. In this case, if a pin hole or a connection in the endoscope is loose, a liquid such as water or a disinfectant may enter the endoscope during washing or disinfection to cause a failure in an electric element such as an optical fiber or a CCD. Thus, to prevent such a failure, a leak test must be carried out on the endoscope.

A common leak test method for an airtight article such as an endoscope comprises immersing the article into water, injecting pressurized air into the article, and checking for bubbles generated. However, this method requires a human operator to execute visual checks and thus fails to automate the leak test. As a result, a manual operation is constantly required.

Thus, it is common to use a method of pressurizing the interior of the endoscope to close up the endoscope and sensing a variation in the internal pressure to determine whether or not there is leakage, as disclosed in Jpn. Pat. Appln. KOKAI Publication No. 5-220110. However, this method requires a pressure sensor (gauge pressure plus absolute pressure) having a full scale for a pressure equal to or higher than that used for the pressurization. If the pressure varies insignificantly in response to leakage, time-consuming measurements are required in order to ensure accuracy.

Thus, Jpn. Pat. Appln. KOKAI Publication No. 4-221733 and Japanese Patent No. 3186438 disclose more accurate and prompt measuring methods based on a method using a differential pressure sensor are disclosed.

However, Jpn. Pat. Appln. KOKAI Publication No. 4-221733 discloses a measuring master (hereinafter referred to as a master) that measures a measured object retaining an initial pressure (the master has a volume almost comparable to that of the measured object). Accordingly, if the measured object is large or has a complicated shape, a considerably high cost is required to produce and maintain the master. Further, it is difficult to reduce the size of the apparatus.

In view of the above disadvantage of Jpn. Pat. Appln. KOKAI Publication No. 4-221733, Japanese Patent No. 3186438 discloses a differential pressure type leak tester that eliminates the need for a master by using a part of a pipe free from leakage, in place of a master.

BRIEF SUMMARY OF THE INVENTION

According to the first aspect of the present invention, there is provided a leak tester which detects leakage of a gas from a measured object, the leak tester comprising:

a source of a pressurized gas which supplies the pressurized gas;

a differential pressure detecting section which detects a pressure difference between the pressure of a gas in the measured object and the pressure of a pressurized gas supplied by the source of the pressurized gas; and a pressure adjusting section which makes the pressure of the pressurized gas supplied by the source of the pressurized gas constant.

According to the second aspect of the present invention which relates to a leak tester according to a first aspect, the leak tester further comprises a pulsation suppressing mechanism which suppresses pulsation of the pressurized gas supplied by the source of the pressurized gas constant.

According to the third aspect of the present invention which relates to a leak tester according to a first aspect, the leak tester further comprises a calculating section which calculates the amount of gas leaking from the measured object on the basis of the pressure difference detected by the differential pressure detecting section and the inner volume of the measured object obtained through input or measurement.

According to the fourth aspect of the present invention which relates to a leak tester according to a third aspect, the leak tester further comprises:

a flow rate detecting section which detects the flow rate of a gas supplied to the interior of the measured object;

a pressure detecting section which detects the pressure of the supplied gas; and an inner volume calculating section which calculates the inner volume of the measured object on the basis of the flow rate detected by the flow rate detecting section and the pressure detected by the pressure detecting section.

According to the fifth aspect of the present invention which relates to a leak tester according to the third aspect, the leak tester further comprises a correcting section which corrects a result of the calculation on the basis of the input or stored amount of gas leaking from the leak tester itself.

According to the sixth aspect of the present invention which relates to a leak tester according to a first aspect, the measured object is an endoscope.

According to the seventh aspect of the present invention which relates to a leak tester according to a sixth aspect, the leak tester further comprises:

an identifying section which identifies the type of the endoscope; and a determining section which determines whether or not a gas is leaking from the endoscope on the basis of the amount of gas leaking based on the pressure difference as well as the type of the endoscope.

According to the eighth aspect of the present invention, there is provided a leak tester which measures pressure leakage from a measured object, the leak tester comprising:

a source of a pressurized gas;

a differential pressure detector which detects a pressure difference between the measured object and an independent closed space; and a pressure adjusting mechanism which keeps a pressure in the independent closed space constant, wherein while the differential pressure detector is detecting the pressure difference, a pressurized gas is introduced into the independent closed space, and the pressure adjusting mechanism keeps the pressure in the independent closed space constant while the pressure difference is being detected.

According to the ninth aspect of the present invention which relates to a leak tester according to the eighth aspect, the source of the pressurized gas is a supplied-gas pump, a pulsation suppressing mechanism is provided between the differential pressure detector and the independent closed space to suppress pulsation of the pressurized gas supplied by the source of the pressurized gas, and while the differential pressure detector is detecting the pressure difference, the supplied-gas pump is activated to introduce the pressurized gas into the independent closed space, and the pressure adjusting mechanism keeps the pressure in the independent closed space constant while the pressure difference is being detected.

According to the tenth aspect of the present invention which relates to a leak tester according to the eighth aspect, before the differential pressure detecting section detects the pressure difference, the measured object and the independent closed space are pressurized to a pressure determined using the pressure adjusting mechanisms.

According to the eleventh aspect of the present invention which relates to a leak tester according to the eighth aspect, the pressure adjusting mechanism includes a relief valve.

According to the twelfth aspect of the present invention which relates to a leak tester according to the ninth aspect, the pulsation suppressing mechanism is a pipe into which a filter is filled.

According to the thirteenth aspect of the present invention which relates to a leak tester according to the ninth aspect, the pulsation suppressing mechanism is a pipe with a reduced diameter.

According to the fourteenth aspect of the present invention which relates to a leak tester according to the eighth aspect, a pressure detector and a flow rate detecting means are disposed in a pipe connected to the measured object, and when the pressure is lower than that determined using the pressure adjusting means, a value for a rise in pressure during a unit time or a predetermined time and the amount of gas flowing into the measured object are detected to infer the inner volume of the measured object on the basis of these values.

According to the fifteenth aspect of the present invention which relates to a leak tester according to the ninth aspect, a pressure detector is disposed in a pipe connected to the measured object, and when the pressure is lower than that determined using the pressure adjusting mechanism, a pressure during a unit time or a predetermined time is detected, a pressure average value and a pressure variation value for the unit time or predetermined time are determined, and the amount of gas flowing into the measured object during the unit time or predetermined time is inferred on the basis of the pressure average value using a known supplied gas amount-ejection pressure characteristic of the supplied-gas pump, and infer the volume of the measured object on the basis of these values.

According to the sixteenth aspect of the present invention which relates to a leak tester according to the eighth aspect, during a step of using the differential pressure detector to detect the pressure difference, leakage from an area formed in the measured object and the independent closed space by closing the on-off valve connected to the measured object, the measured object being excluded from the area, is corrected on the basis of the following equation:

$$Q = V \times \frac{\Delta P}{1.013 \times 10^5} \times \frac{60}{T} - Q_1$$

where Q: the amount of gas leaking from the measured object (ml/min)

V: the volume of the measured object (ml)

$\Delta P$: a pressure difference detected during a time T (Pa)

T: detection time (sec)

$Q_1$: the amount of gas leaking from the leak tester (ml/min).

According to the seventeenth aspect of the present invention which relates to a leak tester according to the eighth aspect, the measured object is an endoscope.

According to the eighteenth aspect of the present invention which relates to a leak tester according to the eighth aspect, the measured object is an endoscope, and the tester has a selecting section which selects a site and/or a series to which the endoscope is applied, and measures pressure leakage on the basis of a pre-stored determination criterion for each applied site and/or series.

DETAILED DESCRIPTION OF THE INVENTION

First Embodiment

A first embodiment of the present invention will be described below with reference to the drawings. The first embodiment relates to a leak tester using a pressurized gas supplied by, for example, a cylinder.

Figure 1:
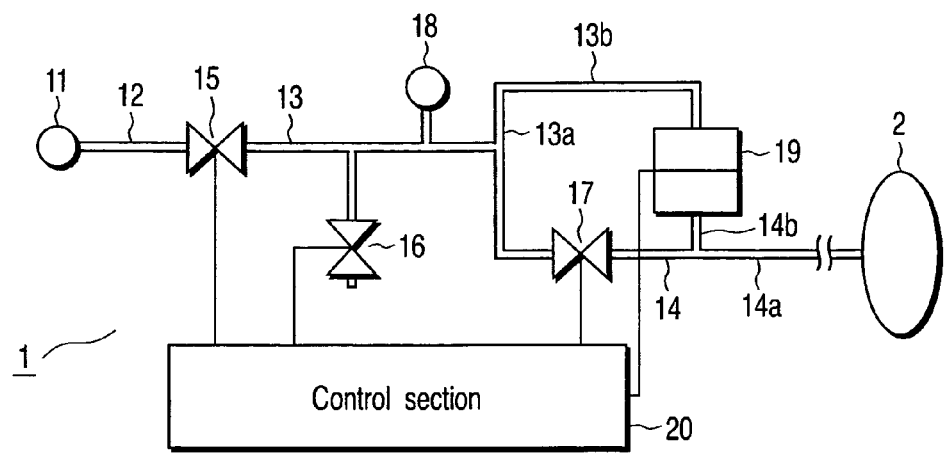
FIG. 1 is a block diagram showing the basic configuration of a leak tester according to a first embodiment of the present invention.

FIG. 1 is a block diagram showing the basic configuration of the leak tester according to the first embodiment. In FIG. 1, a leak tester 1 is composed of a pressurized gas source (a source to supply a pressurized gas) 11, pipes 12 and 13 (including 13a and 13b), a pipe 14 (including 14a and 14b), on-off valves 15, 16, and 17, a relief valve 18, a differential pressure sensor (differential pressure detecting section) 19, and a control section 20 operating as a pressure adjusting section. The pressurized gas source 11 is connected to the on-off valve 15 via the pipe 12. Moreover, the pipe 13 is connected to the on-off valve 15. The pipe 13 branches into two lines and one (pipe 13a) of the lines is connected to the on-off valve 17, while the other (pipe 13b) is connected to the differential pressure sensor 19. The differential pressure sensor 19 detects a pressure difference between the pressure of a gas in a measured object 2 and the pressure of a pressurized gas supplied by the pressurized gas source 11.

Moreover, the on-off valve 17 is connected to the pipe 14. The pipe 14 branches into two lines and one (pipe 14a) of the lines is connected to the washed object 2, while the other line (pipe 14b) is connected to the differential pressure sensor 19. Further, the on-off valve 16 and the relief valve 18 are connected to arbitrary positions of the pipe 13 (including 13a and 13b).

With this configuration, a control section 20 controls the on-off valves 15, 16 and 17 in accordance with the time chart shown in FIG. 2, described later.

Figure 2:
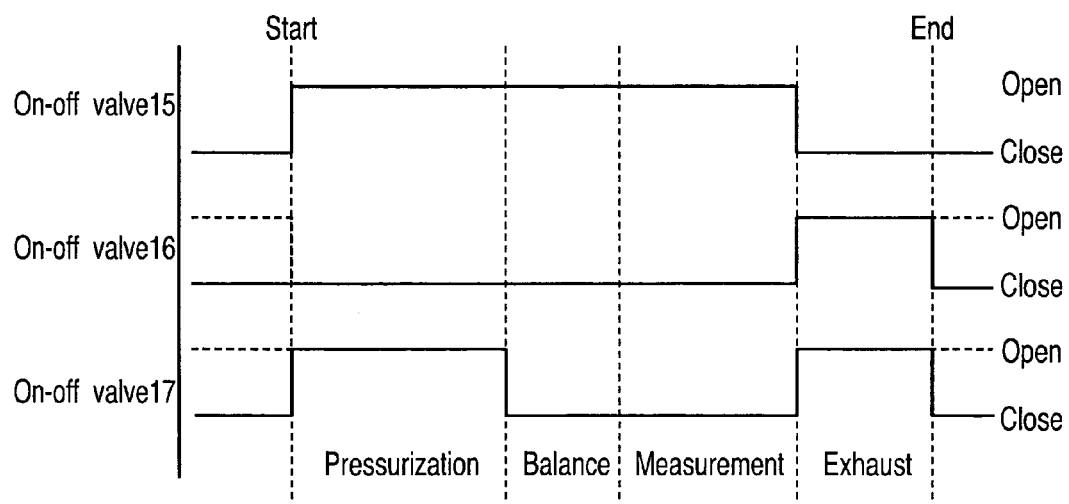
FIG. 2 is a time chart illustrating operations of on-off valves 15, 16, and 17.

FIG. 2 is a time chart illustrating operations of the on-off valves 15, 16, and 17. When a measuring operation is started, a step of pressurizing the interior of the measured object 2 is started. In this step, the control section 20 opens the on-off valves 15 and 17, while closing the on-off valve 16. The relief valve 18 serves to raise the pressurizing pressure up to a specified value to pressurize the measured object 2. A method for the pressurization may be execution of pressurization for a predetermined time or the use of a gauge pressure sensor, described later, for measuring and sensing the pressure.

Then, the control section 20 closes the on-off valve 17 to shift to a balance step. The balance step is intended to gain time until the distribution of the pressure inside the measured object 2 and the pipe 14 becomes uniform. During this step and a measuring step, described later, a gas is continuously supplied to the master. However, in the measured object 2, the on-off valve is closed to form a closed space.

During the balance step and the measuring step, described later, the gas may leak from the relief valve 18. Accordingly, a flow regulating valve (not shown) is preferably disposed in the pipe between the pressurized gas source 11 and the relief valve 18. Further, during this step and the measuring step, described later, the flow regulating valve is preferably activated to reduce the amount of gas supplied and thus gas consumption. However, in this case, the on-off valve 16 is disposed closer to a secondary side (a side that is not the pressurized gas source 11) than the flow regulating valve.

After the balance step has been finished, the process shifts to the measuring step. When the shift occurs, the state of the on-off valves does not change. The control section 20 monitors an output value from the differential pressure sensor 19. The monitoring will be described later in detail.

After the measuring step has been finished, the process shifts to an exhaust step to remove the gas from the measured object 2. The control section 20 closes the on-off valve 15, while opening the on-off valves 16 and 17 to discharge the pressurized gas in the measured object 2 and in the pipes 13 and 14 to the atmosphere. When the exhaust step is ended, the measuring operation is finished.

If the connection between the pipe 14a and the measured object 2 does not include any check valve and disconnection allows the interiors of the measured object and of the line 14a of the leak tester 1 to be opened to the atmosphere, then the exhaust step may be replaced with disconnection of this part. This allows the on-off valve 16 for exhaust to be omitted from the configuration in FIG. 1. In this case, during non-measuring operations (including standby and power-off), the on-off valve 17 is open.

Further, if the measured object 2 is an endoscope and the supplied-gas pump according to the present embodiment is used, the pressurizing step, the balance step, the measuring step, and the exhaust step require 30 seconds, 10 seconds, 10 to 30 seconds, and 5 to 10 seconds, respectively, though the time depends on the volume or shape of the measured object 2, the amount of pressurized air supplied, the pressurization pressure, or the like.

With the above configuration, even if there is leakage from, for example, the connection between the pipe 13 (13a, 13b) and the on-off valve 15, 16, or 17, the relief valve 18, or the differential pressure sensor 19 or these temperatures vary, the interior of the pipe 13 can be maintained at a fixed value determined using the relief valve 18. That is, one input of the differential pressure sensor 19 can be maintained at a fixed value. This makes it possible to simplify a method of connecting the pipe 13 (13a, 13b) to, for example, the on-off valves connected to the pipe 13.

Figure 3:
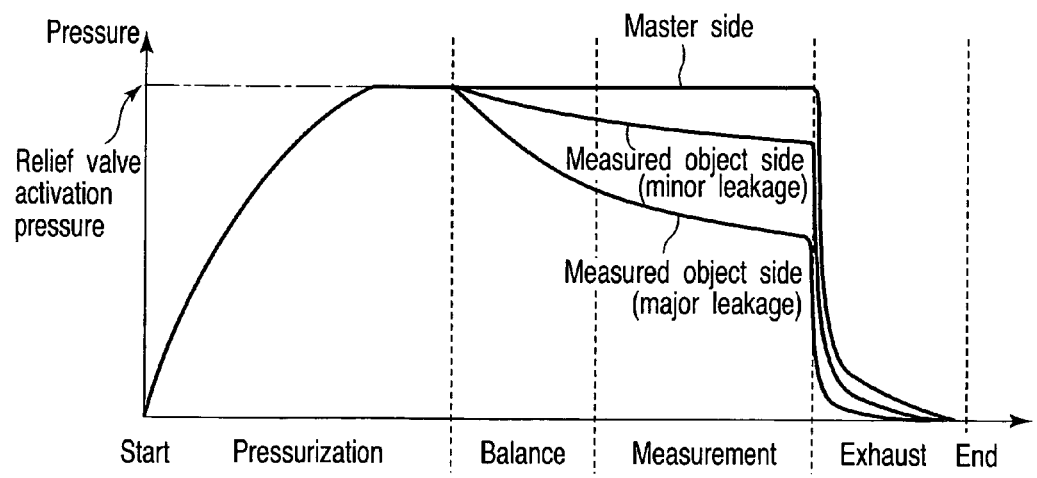
FIG. 3 is a graph showing the transition of the pressure in a pipe 13 (master) and a pipe 14 (measured object) during a measuring operation.
Figure 4:
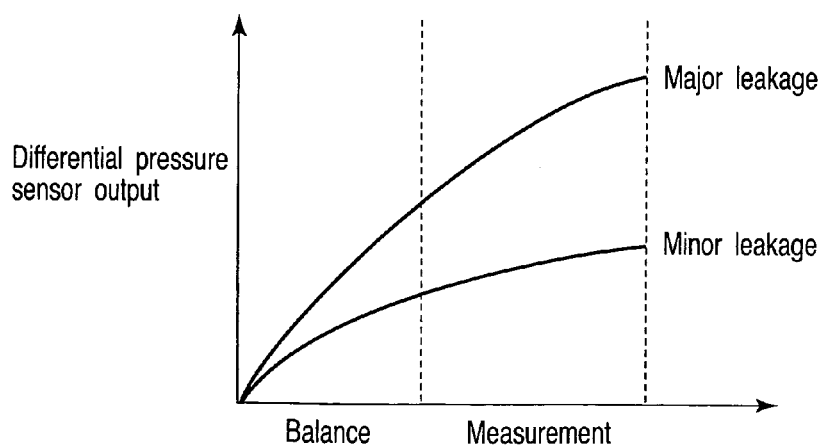
FIG. 4 is a graph showing the transition of output from a differential pressure sensor 19 during a measuring step (including a balance step).

Now, the monitoring will be described. During a measuring operation, the pressures in the pipe 13 (master) and in the pipe 14 (measured object) vary as shown in FIG. 3. Accordingly, during a measuring step (including a balance step), the output from the differential pressure sensor 19 exhibits a characteristic such as the one shown in FIG. 4. The control section 20 retrieves this output value and determines that there is leakage if the amount of variation reaches a predetermined value or more when a unit time or a set time has passed.

The amount of variation at which it is determined that there is leakage must be predetermined. In this case, as shown below by Equation 1, the volume of the measured object 2 may vary the relationship between the amount gas leaking and the amount of variation in pressure. Accordingly, taking this into account, a threshold (the amount of variation or leakage obtained when the unit or predetermined time for determination of the presence or absence of leakage has passed) must be set for each measured object 2.

Moreover, it is necessary to correct leakage from the leak tester itself, that is, leakage from the connection between the pipe 14 (14a, 14b) and the on-off valve 17, the differential pressure sensor 19, or the like. This is because the amount of variation in pressure varies depending on the volume of the measured object 2 in spite of the fixed amount of gas leaking. Thus, if there is leakage from the leak tester 1 itself, the control section 20 must determine the volume of the measured object 2. Of course, the correction is not required if the amount of gas leaking is zero.

In many cases, the thresholds and the amount of gas leaking from the leak tester 1 itself are known. As a common method, a mechanism is provided which allows these values to be manually input to the control section 20 using an input device (such as a keyboard) (not shown) so that it can be determined whether or not there is leakage on the basis of these values.

Of course, the leakage from the leak tester 1 itself is expected to be always fixed. Accordingly, provided that this value is stored in the control section 20, it is normally necessary to input only the thresholds and the volume even if there is no leakage from the leak tester itself. The threshold at which it is automatically determined there is leakage must be determined by substituting the minimum amount of gas leaking at which it is determined that there is leakage into Q in the equation below (Equation 1 or 2). That is, it is determined that there is leakage if a variation in pressure during the unit or predetermined time is at least the threshold. It is determined that there is no leakage if a variation in pressure during the unit or predetermined time is at most the threshold.

$$Q = V \times \frac{\Delta P}{1.013 \times 10^5} \times \frac{60}{T} - Q_1 \quad \text{(Equation 1)}$$

$$\Delta P = \frac{1.013 \times 10^5 \times T}{60 \times V}(Q + Q_1) \quad \text{(Equation 2)}$$
$$= \Delta P_1 + \Delta P_2$$

where Q: the amount of gas leaking from the measured object 2 (ml/min)

V: the volume of the measured object 2 (ml)

$\Delta P$: a pressure difference detected during a time T (Pa)

T: detection time (sec)

$Q_1$: the amount of gas leaking from the leak tester 1 (ml/min)

$\Delta P_1$: a variation in the pressure of the measured object 2 (Pa)

$\Delta P_2$: a variation in the pressure of the leak tester 1 itself (Pa).

In the above equations, the gas is air. $\Delta P_1$ and $\Delta P_2$ vary depending on V.

The amount of actual variation in pressure observed after the unit or predetermined time has passed may be displayed so that on the basis of this value, the user can determine whether or not there is leakage. However, if a simpler system is required, it is also effective to provide a mechanism that automatically measures the volume as described below.

Figure 5:
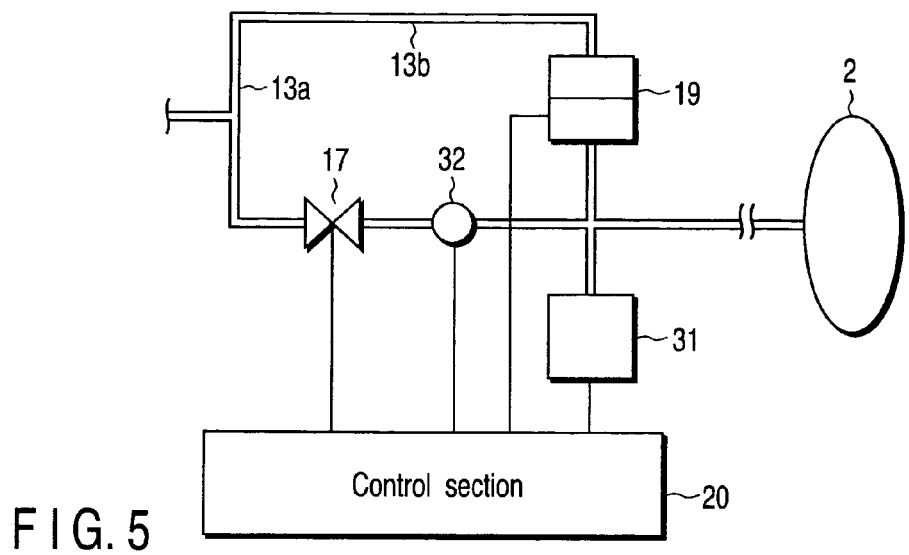
FIG. 5 is a diagram showing a main part of a leak tester having a mechanism that automatically measures volume.
Figure 6:
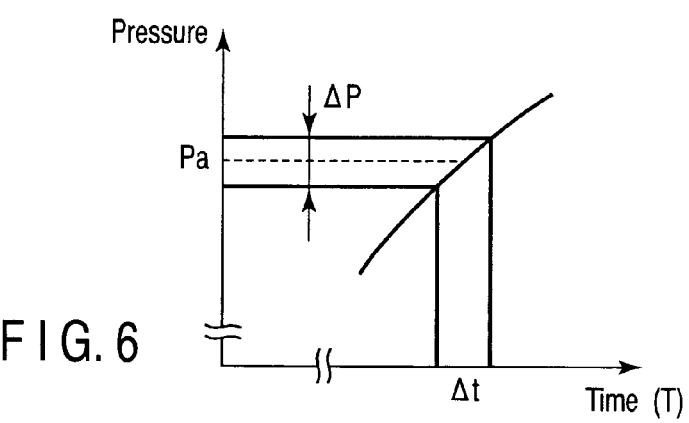
FIG. 6 is a graph illustrating calculation of the volume based on an increase in pressure during a pressurizing step.

FIG. 5 shows the main part of a leak tester having a mechanism that automatically measures the volume. A rise in the pressure varies depending on the volume of the measured object 2. Accordingly, a rise characteristic is measured to calculate the volume. The pressure rises as shown in FIG. 6, but if a rise in temperature per unit time is neglected, the volume of the measured object 2 can be determined using Equation 3, shown below. In this case, the volume of a reference volume retaining section (pipe 13) must be sufficiently low compared to the measured object. The present invention can easily realize this.

$$V = \frac{Pa}{\Delta P}v \quad \text{(Equation 3)}$$

where V: the volume of the measured object (ml),

Pa: the average pressure being measured (Pa)

$\Delta P$: pressure difference (Pa)

v: the amount of gas flowing into the measured object under Pa (ml).

As can be seen in Equation 3, this configuration corresponds to the one shown in FIG. 1 to which a gauge pressure sensor 31 and a flow meter 32 are added. Deservedly, the volume is measured at a pressure equal to or lower than that at which the relief valve 18 is activated. The flow meter 32 may be a current meter. For the current meter, the flow rate is determined by multiplying a measured value by a measurement time.

Of course, the number of criteria for determination of the presence or absence of leakage is not limited to one. It is allowable to use two criteria (no leakage and leakage occurring), three criteria including "determination disabled" in addition to the above two, or four or more criteria. Further, the method of calculation is not limited to the one described above.

The amount of gas leaking from the leak tester 1 itself can be measured by connecting to a master the volume of which is known and which is free from leakage and measuring a pressure difference. This may be carried out during a manufacturing step or during maintenance, with the resulting value written in the control section 20. Compared to the conventional system, which must simultaneously correct leakage in the master, it is only necessary to correct one (leakage from a pipe forming a closed space with the measured object 2 when the on-off valve 17 is closed) of the leakages. Consequently, an accurate system that requires only simple corrections can be provided.

According to the above first embodiment, in the differential pressure type leak tester that does not require any master, the reference pressure is determined using the relief valve. No problem occurs even with a slight leakage from the pipe in the reference pressure retaining section. Further, the pressure is kept constant in spite of a rise in the temperature of the reference pressure retaining section. Consequently, compared to the prior art, in particular, the pipe configuration in the master can be simplified. Since the leak tester is of the differential pressure type, leak tests can be accurately carried out. Furthermore, leakage from the leak tester itself can be corrected using a simple method.

Second Embodiment

Now, a second embodiment of the present invention will be described. The second embodiment relates to a leak tester using a supplied-gas pump, for example, a diaphragm pump.

In the second embodiment, the supply of a pressurized gas is used as the supplied-gas pump. The second embodiment also comprises a mechanism that suppresses pulsation occurring in the supplied-gas pump.

Figure 7:
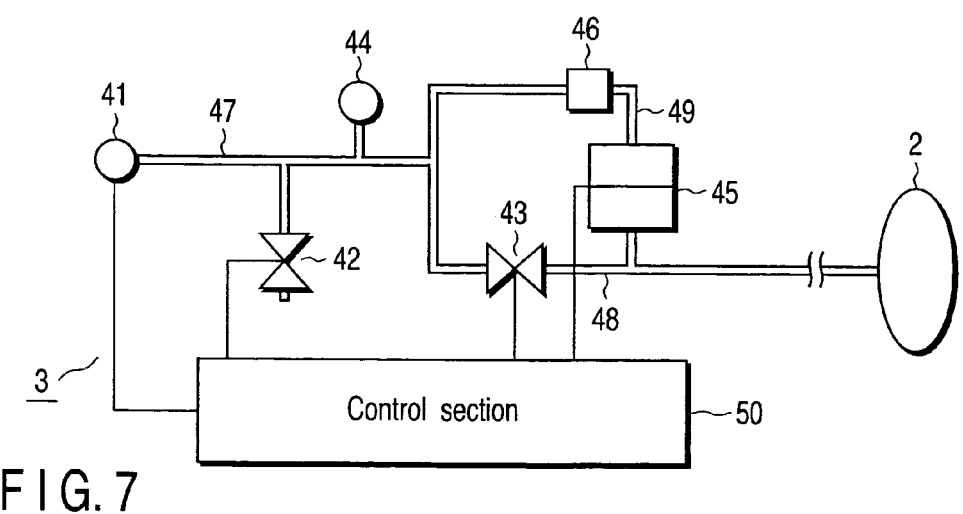
FIG. 7 is a block diagram is a block diagram showing the basic configuration of a leak tester according to a second embodiment of the present invention.

FIG. 7 is a block diagram showing the basic configuration of the leak tester according to the second embodiment. In FIG. 7, the leak tester 3 is composed of a supplied-gas pump 41, on-off valves 42 and 43, a relief valve 44, a differential pressure sensor 45, a pulsation suppressing section 46, pipes 47, 48, and 49, and a control section 50. The description below will focus on parts different from the corresponding ones of the first embodiment. What corresponds to the on-off valve 15 according to the first embodiment is omitted. This is because a comparable operation can be achieved by turning on and off the supplied-gas pump 41. Moreover, the pipe corresponding to the pipe 13b in the first embodiment is connected to the pulsation suppressing section 46. The pulsation suppressing section 46 is connected to the differential pressure sensor 45 via the pipe 49. The operation of the pulsation suppressing section 46 will be described later.

Figure 8:
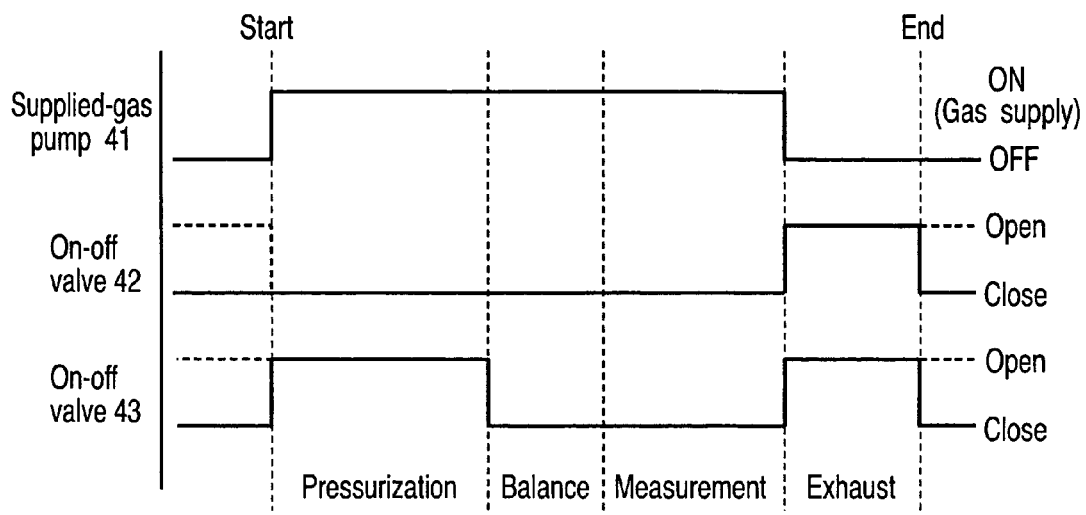
FIG. 8 is a time chart illustrating operations of a supplied-gas pump 41 and on-off valves 42 and 43.

With reference to the time chart in FIG. 8, description will be given of operations of the supplied-gas pump 41 and the on-off valves 42 and 43. Once a measuring operation is started, the control section 50 closes the on-off valve 42, opens the on-off valve 43, and turns on the supplied-gas pump 41 to start a pressurizing step. After the measured object 2 has been pressurized until the pressure determined using the relief valve 44 is reached, the control section 50 closes the on-off valve 43 to shift to a balance step and a measuring step. The operations performed in these steps are essentially similar to those in the first embodiment.

After the measuring step has been finished, the control section 50 opens the on-off valves 42 and 43 and turns off the supplied-gas pump 41 to shift to an exhaust step. After the exhaust has been ended, the measuring operation is finished. Of course, as in the case of the first embodiment, provided that the exhaust is carried out by disconnecting the measured object 2, the exhaust step is not required. In this case, the on-off valve 42 is unnecessary.

A characteristic of the present embodiment is that during the balance step/measuring step, the supplied-gas pump 41 is kept on to supply a gas to the pipes 47 and 49. However, since supplied air is simply discharged from the relief valve, a mechanism that reduces the amount of gas supplied is preferably provided as in the case of the first embodiment. In the present embodiment, it is optimum to reduce the driving force for the supplied-gas pump 41 (if the driving source is a motor, for example, its rotation speed is reduced).

The operation of the pulsation suppressing section 46 will be described below.

In most cases, the supplied-gas pump 41 generally generates pulsation. The pulsation cannot be completely removed using the relief valve 44 but causes a variation of a fixed cycle (the pulsation cycle of the pump) in the pressure applied to the differential pressure sensor 45. That is, a noise of the fixed cycle occurs in the reference pressure. For a system observing a minor difference in pressure, it is a necessary condition that the reference pressure is fixed and this noise is not negligible. Thus, the pulsation suppressing section 46 is provided before an input port of the pulsation sensor 45 to reduce the pulsation-induced noise to a level at which it does not affect measurements.

Figure 9:
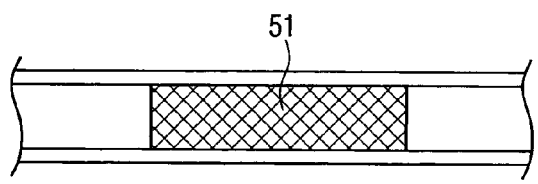
FIG. 9 is a diagram showing an example (1) of the configuration of a pulsation suppressing section 46.
Figure 10:
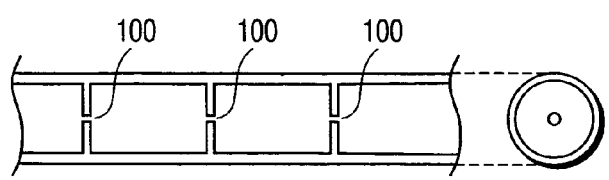
FIG. 10 is a diagram showing an example (2) of the configuration of the pulsation suppressing section 46.

FIGS. 9 and 10 are diagrams showing examples of the configuration of the pulsation suppressing section 46. In FIG. 9, a filter 51 is filled into a part of a line. The suppressing force can be controlled by the amount or density of the filter 51. A specific example of the filter 51 has only to have a resisting action.

In FIG. 10, a mechanism that reduces the diameter of the line is provided. In FIG. 10, three diaphragms 100 are provided, but any number of diaphragms of any diameter can be provided as long as their functions are provided. Of course, as long as the functions are provided, the present embodiment is not limited to these diaphragms. The diaphragms are preferably mounted immediately before the differential pressure sensor 45 so as to avoid affecting the pressurization or exhaust step.

Figure 11:
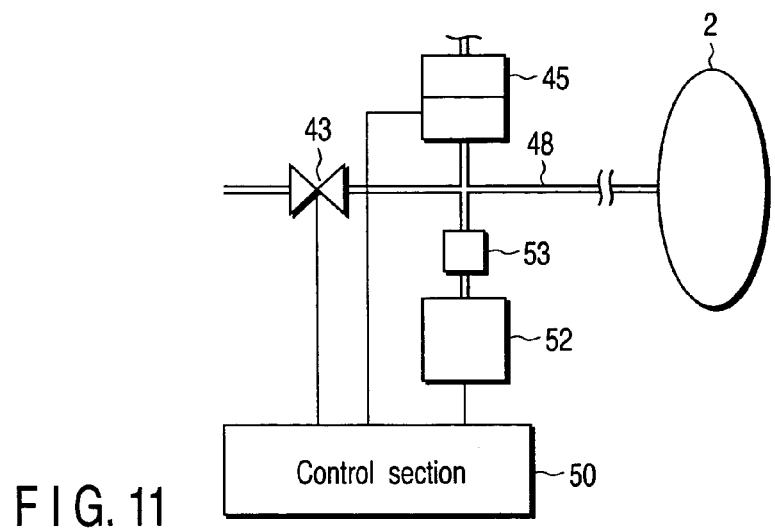
FIG. 11 is a diagram showing a configuration in which only a gauge pressure sensor 52 is connected to a pipe 48 for automatic detection.

If data on the volume of the measured object 2 is automatically detected, the same system as that in the first embodiment is constructed or only the gauge pressure sensor 52 is connected to the pipe 48 as shown in FIG. 11. However, this embodiment differs from the first embodiment in that the pulsation suppressing section 53 is provided before the gauge pressure sensor 52. This is to suppress the input of a pulsation-induced variation in pressure to the sensor as noise. Naturally, the pulsation suppressing sections 46 and 53 need not exert the same suppressing force but may exert different suppressing forces adapted to the respective sensors.

Description will be given below of a method of calculating the volume if the gauge pressure sensor 52 and the pulsation suppressing section 53 are provided as shown in FIG. 11.

Figure 12:
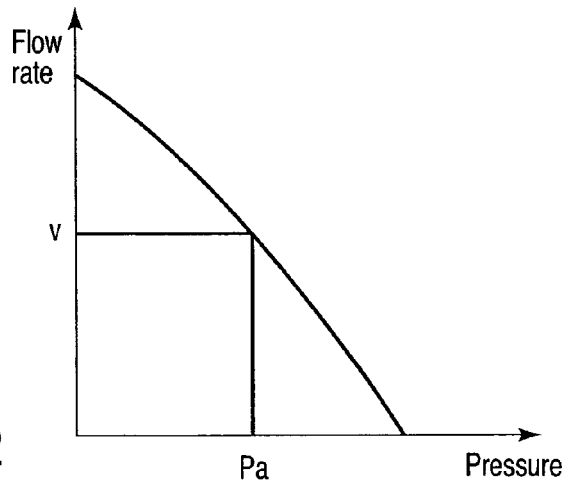
FIG. 12 is a graph showing the supplied-gas characteristic of the supplied-gas pump.

The gas supplying capability (pressure-flow rate characteristics) of the supplied-gas pump used has characteristics such as those shown in FIG. 12 and is known. During a pressurizing process, output from the gauge pressure sensor 52 per unit (predetermined) time is monitored to calculate a pressure average value Pa and a pressure rise value ΔP per unit (predetermined) time. The characteristic value in FIG. 12 is stored in the control section 50 as a known value. Accordingly, the flow rate v per unit (predetermined) time at the pressure average value Pa can be calculated from the characteristic value. Consequently, the volume of the measured object 2 can be calculated using Equation 3 as in the case of the first embodiment.

Description will be given of an auto leak tester for an endoscope having the functions described below.

Figure 13:
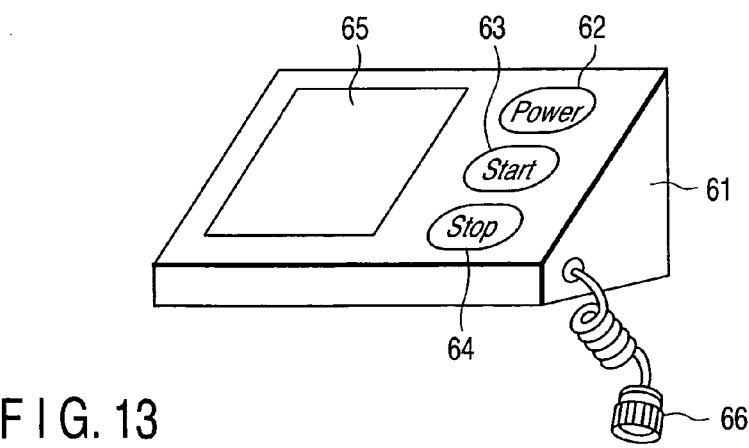
FIG. 13 is a diagram showing the appearance of an auto leak tester for an endoscope.

FIG. 13 is a diagram showing the appearance of the auto leak tester for an endoscope. A main body 61 is provided with a power SW 62, a start SW 63, a stop SW 64, a display section 65, and an endoscope connection connector 66.

Figure 14:
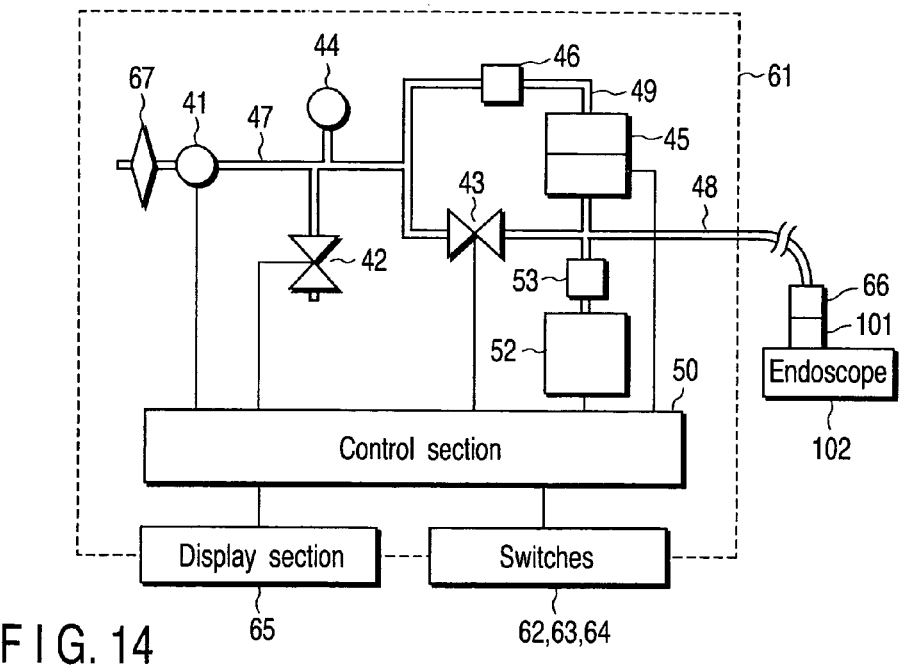
FIG. 14 is a diagram showing the internal structure of the auto leak tester for an endoscope.

FIG. 14 is a diagram showing the internal structure of the auto leak tester for an endoscope. This configuration is basically the same as that shown in FIG. 7. Reference numeral 67 denotes a filter disposed in order to prevent suction of contaminants. The control section 50 connects to the above display section 65 and various switches 62, 63, and 64. Moreover, the endoscope connection connector 66 connects to leakage check connector 101 connected to the space in the endoscope 102.

In view of the fact that the measured object is the endoscope, the volume of the endoscope can be grouped on the basis of a target site used (stomachache, duodenum, large intestine, bronchi, or the like) or functions (fibers, CCD, and ultrasonic waves). Accordingly, volume/threshold information for each group may be stored in the control section 50 so that the volume information can be determined by manually selecting a particular group.

Figure 15:
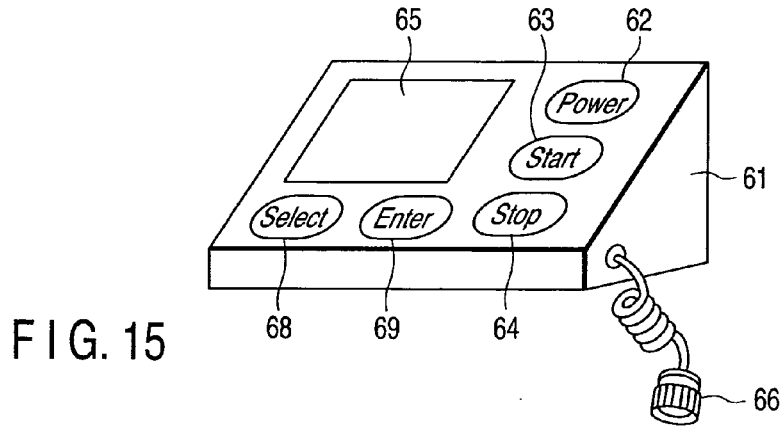
FIG. 15 is a diagram showing the appearance of a leak tester for an endoscope with a scope selector function.

FIG. 15 is a diagram showing the appearance of the leak tester for an endoscope in this case. In addition to the configuration shown in FIG. 13, a selector SW 68 and a determination SW 69 are added. Further, a barcode for the endoscope or the like may be applied and a reading device (not shown) and the leak tester may be coupled together so that scope classification can be carried out.

However, the same amount gas leaking can normally be set as a threshold in most groups. Accordingly, the above automatic volume measuring function may be used to measure the volume so that a threshold (the amount of variation in pressure) can be calculated from a threshold (the amount gas leaking) to determine whether or not there is leakage.

Alternatively, data on the volume of the endoscope 102 or the amount of variation in pressure (unit or predetermined time) may be stored in the endoscope 102 so that when the endoscope 102 is connected to the auto leak tester, the auto leak tester reads the data stored in the endoscope 102. This system can be utilized to construct a system which can suppress variations and deal easily with new endoscopes.

Description will be given of the leak tester for an endoscope having an automatic volume measuring function. Since the endoscope 102 is formed of resin or rubber, a rise in pressure may destroy the endoscope 102. Consequently, the pressure applied is lower than that for general measured objects. Specifically, the pressurization is desirably carried out at a pressure of 0.3 to 0.4 kg/cm$^2$.

Further, the endoscope 102 is shaped like an elongate pipe and has a narrow gap inside. The endoscope 102 is thus characterized in that a long time is required to uniformly pressurize the interior of the endoscope 102. Thus, the pressurization is preferably sustained for some time even after a predetermined pressure is reached during a pressurizing step. Likewise, the exhaust is preferably sustained for a longer time.

Since the endoscope 102 has such characteristics, the leak tester for an endoscope operates as follows:

1) Preparing Step

A waterproof connector is connected to the endoscope 102 to make it waterproof if required. The endoscope connection connector 66 is attached to the leakage check connector 101 of the endoscope 102. Further, when the endoscope 102 is touched or moved during measurements, the internal pressure may vary. Accordingly, a method is used which comprises, for example, placing the endoscope 102 in a stable area or hanging it on a hanger.

2) Pressurizing Step

After pressurization has been started, the volume is measured as previously described. At the same time, the gauge pressure sensor 52 is used to detect whether or not a predetermined pressure (for example, 0.3 to 0.4 $kg/cm^2$) has been reached. If the predetermined pressure is not reached even after a predetermined time (for example, 30 seconds to 1 minute) has elapsed, it is determined that there is a defect in the leak tester, the connection between the leak tester and the endoscope 102 is inappropriate, or there is a marked leakage from the endoscope 102. Then, the process is shifted to an exhaust step. Subsequently, the operation is stopped and a warning is displayed. If the predetermined pressure is reached within the predetermined time, the pressurization is further sustained for a predetermined time (for example, 5 to 10 seconds).

3) Balance Step

The process waits for the pressure in the endoscope 102 to become uniform (for example, 10 seconds). Even during this step, the gauge pressure sensor 52 is used to measure the pressure to check whether or not there is a marked leakage. If there is a marked leakage, the process shifts to an exhaust step. Subsequently, the operation is stopped and a display is provided showing that there is leakage.

4) Measuring Step

If the gauge pressure sensor 52 is used to measure the pressure to find that there is a variation of a predetermined value in pressure (already corrected), the process shifts to an exhaust step. Subsequently, the operation is stopped and a display is provided showing that there is leakage. If a variation of at least the predetermined value is not detected even after a predetermined time (for example, 10 to 30 seconds) has elapsed, it is determined that there is no leakage. Then, after the exhaust step described below, a display is provided showing that there is no leakage.

5) Exhaust Step

After a predetermined time (for example, 5 to 10 seconds) has elapsed, the process returns to a standby state.

According to the above second embodiment, the supplied-gas pump is used as the pressurized gas source in the first embodiment, and the mechanism is provided which suppresses a variation in pressure caused by pulsation from the supplied-gas pump. This eliminates the need to connect to a gas cylinder or the like, while utilizing the characteristics of the first embodiment. It is also easier to reduce the size of the apparatus by, for example, reducing the number of on-off valves. Furthermore, a simpler system can be constructed.

Figure 16:
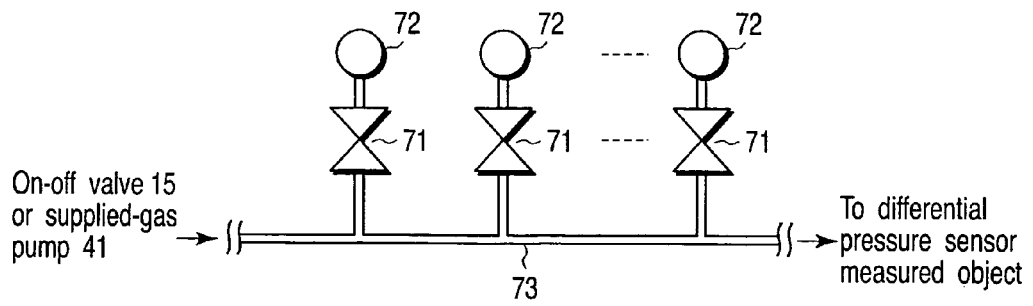
FIG. 16 is a main block diagram showing the case in which a plurality of relief valves are provided.

In the above first and second embodiments, the number of relief valves need not be one. The pressurization pressure can be selected in accordance with the measured object by providing a plurality of (at least two) relief valves. That is, it is contemplated that on-off valves 71, 71, . . . may be disposed between a pipe 73 and relief valves 72, 72, . . . having different relief pressures and may be selectively opened and closed as shown in FIG. 16.

Further, although not shown, a relief valve may be used which has a relief pressure adjusting function. In this case, the pressurization pressure for the measured object 2 is manually adjusted. In this case, a gauge pressure sensor such as those shown in FIGS. 5 and 11 is preferably added so that the leak tester displays the pressurization pressure.

The relief valves generally do not exhibit a completely fixed value but their pressure value varies slightly depending on the amount of gas relieved or the like; for example, the pressure at which the valves start to open is, for example, 98% of a rated value. However, the pressure value is stabilized provided that the amount of gas relieved is fixed. Thus, no problem occurs during the measuring step (including a balance step) in the present system. In this case, there may be a mismatch with the pressure value during pressurization. However, this also does not pose any problem because the present system measures a varying value, so that the initial value need not be zero.

As described above, if the pressurization pressure is changed, the amount of gas leaking from the auto leak tester itself also changes. Consequently, accurate sensing can be accomplished by measuring the amount of gas leaking at a set pressure and storing or manually inputting the measured amount.

The present invention is not limited to the illustrated components. Other components may be used as long as they provide required functions.

(Appendix)

1) A leak tester which measures a pressure leakage from a measured object by detecting a pressure difference between the measured object and an independent closed space, characterized by:

comprising a source of a pressurized gas, a differential pressure detector, on-off valves, and pipes, as well as pressure adjusting means provided in the independent closed space for keeping a pressure in the space constant, and in that while the pressure difference is being detected, a pressurized gas is introduced into the independent closed space, and the pressure adjusting means keeps the pressure in the independent closed space constant while the pressure difference is being detected.

2) A leak tester which measures a pressure leakage from a measured object by detecting a pressure difference between the measured object and an independent closed space, characterized by:

comprising a supplied-gas pump, a differential pressure detector, on-off valves, and pipes, as well as pressure adjusting means provided in the independent closed space for keeping a pressure in the space constant and pulsation suppressing means disposed between the differential pressure detector and the independent closed space, and in that while the pressure difference is being detected, the supplied-gas pump is activated to introduce a pressurized gas into the independent closed space, and the pressure adjusting means keeps the pressure in the independent closed space constant while the pressure difference is being detected.

3) The leak tester according to 1) or 2), characterized in that before the pressure difference is measured, the measured object and the independent closed space are pressurized to a pressure determined using the pressure adjusting means.

4) The leak tester according to any of 1), 2), and 3), characterized in that the pressure adjusting means is a relief valve.

5) The leak tester according to 2), characterized in that the pulsation adjusting means is a pipe into which a filter is filled.

6) The leak tester according to 2), characterized in that the pulsation adjusting means is a pipe with a reduced diameter.

7) The leak tester according to 1) or 2), characterized in that a pressure detector and a flow meter detecting means are disposed in a pipe connected to the measured object, and means is provided which operates when the pressure is lower than that determined using the pressure adjusting means, to detect a value for a rise in pressure during a unit time or a predetermined time and the amount of gas flowing into the measured object and infer the inner volume of the measured object on the basis of these values.

8) The leak tester according to 2), characterized in that a pressure detector is disposed in a pipe connected to the measured object, and means is provided which operates when the pressure is lower than that determined using the pressure adjusting means, to detect a pressure during a unit time or a predetermined time, determine a pressure average value and a pressure variation value for the unit time or predetermined time, infer the amount of gas flowing into the measured object during the unit time or predetermined time, from the pressure average value on the basis of a known supplied gas amount-ejection pressure characteristic of the supplied-gas pump, and infer the volume of the measured object on the basis of these values.

9) The leak tester according to 1) or 2), characterized in that during a step of detecting a pressure difference, leakage from an area which forms a closed space with the measured object when the on-off valve connected to the measured object is closed, the measured object being excluded from the area, is corrected on the basis of the following equation:

$$Q = V \times \frac{\Delta P}{1.013 \times 10^5} \times \frac{60}{T} - Q_1$$

where Q: the amount of gas leaking from the measured object (ml/min)

V: the volume of the measured object (ml)

$\Delta P$: a pressure difference detected during a time T (Pa)

T: detection time (sec)

$Q_1$: the amount of gas leaking from the leak tester (ml/min).

10) The leak tester according to any of 1) to 9), characterized in that the measured object is an endoscope.

11) The leak tester according to 1) or 2), characterized in that the measured object is an endoscope, and the tester has means for selectively identifying a site and/or a series to which the endoscope is applied, and measures a pressure leakage on the basis of a pre-stored determination criterion for each applied site and/or series.

In the above configuration, 1), and 3), 4), 7), and 9) consist of the source of a pressurized gas, the differential pressure sensor, a first and second pipes, a first to third on-off valves, and the relief valve. The source of a pressurized gas is connected to an input port of the first on-off valve. The first pipe is connected to an output port of the first on-off valve. The first pipe further branches into two lines. One of the lines is connected to one port of the differential pressure sensor. The other line is connected to an input port of the second on-off valve. The relief valve and the third on-off valve are connected to arbitrary positions of the first pipe. The second pipe is connected to the measured object and also branches into two lines. One of the lines is connected to one port of the differential pressure sensor. The other line is connected to an output port of the second on-off valve.

With the above configuration, the pressure difference is measured by maintaining the pressure determined using the relief valve, in the first pipe rather than maintaining a closed pressurization pressure in a part of the master or pipe.

Further, 2) and 3) to 9) are characterized in that compressed air from the supplied-gas pump is used as a pressurized gas and in that not only the above configuration is provided except for the first on-off valve but pulsation suppressing means for suppressing pulsation from the supplied-gas pump is also disposed at or immediately before a connection between the first pipe and the port of the differential pressure sensor.

The above configuration measures the pressure difference by using diaphragms or the like to suppress the adverse effect of a pulsation-induced variation in pressure on detection by the differential pressure sensor.

In any of the above cases, for more accurate leakage measurements, determination is made by calculating the amount of gas leaking on the basis of information on the volume of the measured object and a value for a variation obtained by the differential pressure sensor. Of course, determination may be made on the basis of only the variation value and without the amount of gas leaking.

Further, 7) and 8) are characterized in that the volume of the measured object is automatically measured in order to accomplish more accurate leakage measurements and in that not only the above configuration is provided but a gauge pressure sensor (or an absolute pressure sensor) is also connected to the second pipe.

Moreover, 9) is characterized in that a function to correct leakage from the leak tester itself is provided to the above configuration.

In 10) and 11), the measured object is limited to the endoscope. Leakage checks are executed on the basis of conformable data by pre-storing volume information and determination criteria in the apparatus and inputting the type of the endoscope.

The above configuration enables leakage to be accurately sensed using simple arrangements.

According to the present invention, a leak tester is provided which enables leakage to be accurately sensed using simple arrangements.

What is claimed is:

1. A leak tester which detects leakage of gas from a measured object, the leak tester comprising:
   a source of a pressurized gas which supplies the pressurized gas;
   a first pipe through which the pressurized gas from the source flows;
   a second pipe which communicates with the first pipe and through which the pressurized gas flows, the second pipe being branched from the first pipe, communicating with the measured object, and allowing the pressurized gas to flow in the measured object;

an on-off valve, which is interposed between the second pipe and the measured object, and stops flow of the pressurized gas into the second pipe in accordance with opening and closing action of the on-off valve, the on-off valve stopping the flow of the pressurized gas into the measured object when closed;

a third pipe, which communicates with the second pipe, and which is branched from the second pipe and interposed between the measured object and the on-off valve;

a differential pressure detecting section which is connected to the first pipe and the third pipe, and detects a pressure difference over a predetermined time between the pressure of the pressurized gas supplied to the first pipe, and the pressure of the pressurized gas supplied in the measured object, the pressure difference being detected when the on-off valve is closed, and the pressure of the pressurized gas supplied in the measured object being defined based on the pressure of the pressurized gas supplied to the third pipe; and a pressure adjusting mechanism which adjusts the pressure in the first pipe to make the pressure of the pressurized gas in the first pipe constant, the pressure adjusting mechanism comparing the pressure difference detected by the differential pressure detecting section to a threshold pressure difference to detect said leakage, the threshold pressure difference determined by taking into account leakage of gas from the leak tester and based on the volume of the measured object.

2. The leak tester according to claim 1, further comprising a calculating section which calculates the amount of gas leaking from the measured object on the basis of the pressure difference detected by the differential pressure detecting section and inner volume of the measured object obtained through input or measurement.

3. The leak tester according to claim 1, wherein before the differential pressure detecting section detects the pressure difference, the pressure of the gas in the measured object and the pressure of the gas in the first pipe are pressurized to a pressure determined by the pressure adjusting mechanism.

4. The leak tester according to claim 1, wherein the pressure adjusting mechanism includes a relief valve, which keeps the pressure of the gas in the first pipe at a predetermined pressure, while the differential pressure detecting section is detecting the pressure difference.

* * * * *